United States Patent
Weisbeck et al.

(10) Patent No.: US 6,734,133 B1
(45) Date of Patent: May 11, 2004

(54) SURFACE-MODIFIED MIXED OXIDES CONTAINING PRECIOUS METAL AND TITANIUM, FOR THE SELECTIVE OXIDATION OF HYDROCARBONS

(75) Inventors: Markus Weisbeck, Köln (DE); Christoph Schild, Leverkusen (DE); Gerhard Wegener, Mettmann (DE); Georg Wiessmeier, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/980,603

(22) PCT Filed: Apr. 18, 2000

(86) PCT No.: PCT/EP00/03491

§ 371 (c)(1),
(2), (4) Date: Feb. 21, 2002

(87) PCT Pub. No.: WO00/64582

PCT Pub. Date: Nov. 2, 2000

(30) Foreign Application Priority Data

Apr. 23, 1999 (DE) .......................... 199 18 431

(51) Int. Cl.⁷ .......................... C04B 35/03; C04B 35/04
(52) U.S. Cl. .................................... 502/119
(58) Field of Search ........................ 502/119

(56) References Cited

U.S. PATENT DOCUMENTS

| | | | |
|---|---|---|---|
| 3,923,843 A | 12/1975 | Wulff | 260/348.5 L |
| 5,703,254 A | 12/1997 | Gaffney et al. | 549/536 |
| 5,760,254 A | 6/1998 | Grey | 549/532 |
| 5,763,630 A | 6/1998 | Kahn et al. | 549/534 |
| 5,840,650 A | 11/1998 | Tamura et al. | 502/350 |

FOREIGN PATENT DOCUMENTS

| | | |
|---|---|---|
| EP | 0 827 779 | 3/1998 |
| EP | 1 005 907 | 6/2000 |
| WO | 98/00413 | 1/1998 |
| WO | 98/00414 | 1/1998 |
| WO | 98/00415 | 1/1998 |
| WO | 99/26936 | 6/1999 |
| WO | 99/39826 | 8/1999 |

OTHER PUBLICATIONS

Catal. Rev. –Sci. Eng., 23(1&2), pp. 127–149 (month unavailable) 1981 On the Mechanism of Ethylene Epoxidation by Sachtler et al.

*Primary Examiner*—Taofiq Solola
(74) *Attorney, Agent, or Firm*—Joseph C. Gil; John E. Mrozinski, Jr.

(57) ABSTRACT

This invention relates to a process for the production of a composition containing gold and/or silver particles, mixed oxides containing titanium and silicon which have been surface-modified, to the compositions producible in this process and to the use thereof in processes for the selective oxidation of hydrocarbons in the presence of oxygen and a reducing agent. The catalytically active compositions exhibit constantly high selectivities and productivities.

16 Claims, 1 Drawing Sheet

US 6,734,133 B1

SURFACE-MODIFIED MIXED OXIDES CONTAINING PRECIOUS METAL AND TITANIUM, FOR THE SELECTIVE OXIDATION OF HYDROCARBONS

This application is a 371 of PCT/EP00/03491 filed Apr. 18, 2000.

TECHNICAL FIELD OF THE INVENTION

This invention relates to a process for the production of a composition containing gold and/or silver particles, mixed oxides containing titanium and silicon which have been surface-modified, to the compositions producible in this process and to the use thereof in processes for the selective oxidation of hydrocarbons in the presence of oxygen and a reducing agent. The catalytically active compositions exhibit constantly high selectivities and productivities.

BACKGROUND OF THE INVENTION

The direct oxidation of ethene to yield ethene oxide by molecular oxygen is well known and is used for the commercial production of ethene oxide in the gas phase. The typical catalyst for this application contains metallic or ionic silver, possibly additionally modified with various promoters and activators. Most such catalysts contain a porous, inert catalyst support having a small surface area, such as for example alpha-aluminium oxide, onto which the silver and promoters have been applied. A review of the direct oxidation of ethene in the presence of supported silver catalysts has been compiled by Sachtler et al. in *Catalysis Reviews: Science & Engineering*, 23 (1&2), 127–149 (1981).

It is also known that these silver catalysts and the reaction conditions which have proved favourable for ethene oxide production do not give rise to comparably good results in the direct oxidation of higher olefins, such as propene (U.S. Pat. Nos. 5,763,630, 5,703,254, 5,760,254) and propene oxide selectivities of at most approx. 50% are achieved. In general, direct oxidation reactions of these higher olefins with molecular oxygen do not generally proceed in the gas phase at below 200° C., even in the presence of catalysts, and the selective production of oxidation products sensitive to oxidation, such as epoxides, is thus difficult as the consecutive reactions of these products frequently proceed more rapidly than the oxidation of the introduced olefins themselves. Another problem arises from the sensitivity to oxidation of the allyl groups present in higher olefins.

For this reason, only indirect, liquid phase methods are currently used for the industrial production of propene oxide.

Some 50% of propene oxide output worldwide is currently produced using the "chlorohydrin process", while another 50%, with a rising trend, is produced by the "oxirane process".

In the chlorohydrin process (Weissermel et al. in *Industrielle organische Chemie*, 4$^{th}$ edition, Weinheim, 1994, pages 288–289), chlorohydrin is first formed by reacting propene with HOCl (water and chlorine) and the propene oxide is then formed therefrom by elimination of HCl with a base. The process is cost-intensive but, when properly optimised, exhibits high selectivity (>90%) with elevated conversions. The loss of chlorine in the chlorohydrin process in the form of worthless calcium chloride or sodium chloride solutions and the associated high waste water salt loads quickly led researchers to seek out chlorine-free oxidation systems.

The oxirane process (Weissermel et al. in *Industrielle organische Chemie*, 4$^{th}$ edition, Weinheim, 1994, pages 289–291), uses organic compounds to transfer oxygen onto propene instead of the inorganic oxidising agent HOCl. This indirect epoxidation is based on the fact that organic peroxides such as hydroperoxides in the liquid phase are capable of selectively transferring their peroxide oxygen onto olefins to form epoxides. This reaction converts the hydrogen peroxides into alcohols and the peroxycarboxylic acids into acids. Hydroperoxides are produced from the corresponding hydrocarbon by autoxidation with air or molecular oxygen. One serious disadvantage of indirect oxidation is the economic dependency of the value of propene oxide on the market value of the co-product and the cost-intensive production method for the oxidising agents.

There is currently no industrial gas phase process for the direct oxidation of propene to yield propene oxide.

Catalysts are known in which gold particles are applied onto a support consisting of dispersed titanium centres on a silicon matrix (WO 98 00415 A1; WO 98 00414 A1; EP 0 827 779 A1). All these materials obtained by impregnation with subsequent calcination become deactivated over time (typical half-lives are 5–50 h) and thus cannot be used in large scale industrial plants.

Further catalysts are also known in which gold particles are applied onto microporous, crystalline tectosilicates having a defined pore structure, in which silicon tetrahedron sites are isomorphically substituted by titanium (for example TS-1, TS-2, Ti zeolites, such as Ti-beta, Ti-ZSM-48 or mesoporous molecular sieves containing titanium, such as for example Ti-MCM-41 or Ti-HMS) (WO 9800413 A1). While all these gold silicalite or gold zeolite structures do indeed exhibit good selectivities, the hydrocarbon conversion rates and, most particularly, the catalyst service lives are completely inadequate for use in the chemicals industry.

The described processes for catalyst preparation are highly unsatisfactory with regard to catalyst activity and service life. Industrial processes operating with low activity catalysts require enormous reactors. Low catalyst service lives entail production downtime during the regeneration phase or demand cost-intensive redundant plant design. It is thus desirable to develop catalysts which can achieve elevated levels of activity combined with excellent selectivity and industrially useful service lives.

SUMMARY OF THE INVENTION

One object of the present invention was accordingly to provide a technically straightforward catalytic gas phase process for the selective oxidation of hydrocarbons using a gaseous oxidising agent on low cost solid catalysts, which process combines very high selectivities and industrial useful catalyst service lives with high yields and low costs.

A further object of the invention was to provide catalysts having better service lives.

A further object of the invention was to provide a process which yields catalysts having better service lives.

The objects are achieved according to the invention by a supported composition containing gold and/or silver particles, titanium oxide and a support containing silicon, characterised in that the surface of the composition bears groups selected from among alkylsilicon, arylsilicon, alkyl groups containing fluorine or aryl groups containing fluorine.

DETAILED DESCRIPTION OF THE INVENTION

Figure 1:
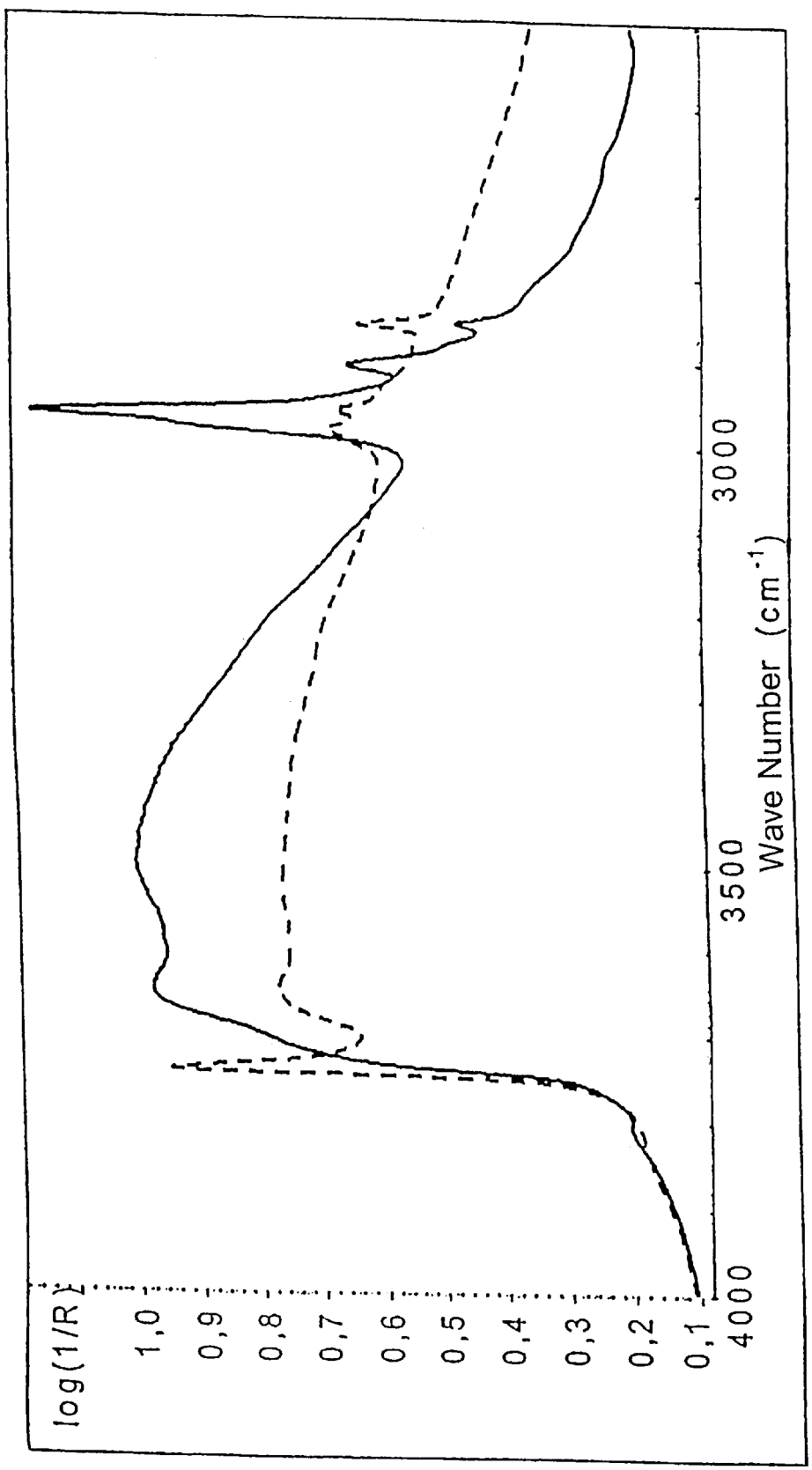
FIG. 1 illustrates the DRIFTS spectrum of two silylated and unsilylated materials, which were produced according to Example 1.

The supported composition according to the invention contains gold and/or silver on a support material. In the catalytically active state, gold and/or silver is primarily present as elemental metal (analysis by X-ray absorption spectroscopy). Small proportions of gold and/or silver may also be present in a higher oxidation state. On the basis of TEM micrographs, the largest proportion of the gold and/or silver present is on the surface of the support material in the form of nanometer-scale gold and/or silver clusters. The gold particles preferably have a diameter in the range from 0.5 to 50 nm, preferably from 0.5 to 15 nm and particularly preferably of 0.5 to 10 nm. The silver particles preferably have a diameter in the range from 0.5 to 100 nm, preferably from 0.5 to 40 nm and particularly preferably of 0.5 to 20 nm.

The gold concentration should be in the range from 0.001 to 4 wt. %, preferably from 0.001 to 2 wt. % and particularly preferably from 0.005–1.5 wt. % of gold.

The silver concentration should be in the range from 0.005 to 20 wt. %, preferably from 0.01 to 15 wt. % and particularly preferably from 0.1 to 10 wt. % of silver.

Gold and/or silver concentrations higher than the stated ranges do not increase catalytic activity. On economic grounds, the noble metal content should be the minimum quantity required to achieve maximum catalyst activity.

The crystal structure of the titanium oxide and/or titanium/silicon mixed oxide is, in principle, freely selectable, but the amorphous modification and the crystalline anatase and/or Si—O—Ti mixed oxide modification are preferred. The titanium oxide need not be present as a pure component, but may also assume the form of a complex material, for example in combination with other oxides (for example titanates). As far as we are aware and without wishing to restrict the invention in any way, it is in particular the titanium centres which are chemically attached to silica and/or inorganic silicates which constitute the catalytically active centres. We furthermore assume that in active catalysts, titanium is attached to the silica or silicate in the form of the oxide [for example —Si—O—Ti(=O)—O—Si—].

The catalytic activity of these materials apparently cannot be raised in a linear manner in accordance with the total titanium oxide content if the titanium oxide content is >4–6 mol %. This showed us that not all the titanium centres have the same catalytic activity. In general terms, it is desirable to produce a catalyst having the greatest possible activity, measured as the selectively formed oxidation product per unit time for a given weight of catalyst. The presence of titanium atoms which are catalytically inert or facilitate unwanted secondary reactions, for example combustion of hydrogen, or the formation of other unwanted oxidation products gives rise to catalyst systems having non-optimal catalyst activity.

The support materials containing silicon according to the invention advantageously consist of 50%, preferably of 75% and particularly preferably of >90% of the oxide form of silicon. The support materials containing silicon according to the invention may also contain, apart from silicon dioxide and silicates, other oxides, for example aluminium oxide, zirconium oxide etc. Support materials containing silicon having a large specific surface area and a large proportion of surface silanol groups are preferably used. The specific surface area should be at least 1 m²/g, preferably in the range from 25–700 m²/g.

Preferred support materials containing silicon are synthetically produced porous silicon dioxides such as for example silica gels, precipitated silica, precipitated silica gels, silicalites or the like and mixtures thereof. Production methods for such synthetically produced silicas are described in *The Colloid Chemistry of Silica and Silicates* (R. G. Iler, Cornell University Press, New York, USA, 1955, Chapter VI). Examples of these silicas are pyrogenic silicas which are obtained by reacting silicon tetrachloride or tetrafluoride with hydrogen and oxygen (for example Cab-o-sils from Cabot Corporation or Aerosils from Degussa).

Crystalline aluminosilicates and silicalites, known as molecular sieves, such as faujasite, mordenite, beta, ZSM-3, ZSM 5, ZSM-11, ZSM 12, ZSM 18, ZSM 20, ferrierite, MCM-22, MCM-41, MCM-48, MCM-56 etc., may also be used as support materials containing silicon. Naturally occurring crystalline silicates may also be used, in particular serpentine (magnesium silicate), clay minerals such as hectorite (lithium/magnesium silicate), kaolin, bentonites and mica minerals such as phlogopite (aluminium/magnesium/potassium silicalite) or similar materials.

Of the stated support materials containing silicon, the synthetically produced amorphous silicas and/or silicalites are particularly preferred. Support materials containing silicon having an SiOX content of >90% are particularly preferred.

In addition to titanium, the compositions according to the invention may contain further foreign oxides, so-called promoters, from group 5 of the IUPAC periodic system (1985), such as vanadium, niobium and tantalum, preferably tantalum, from group 3, preferably yttrium, from group 4, preferably zirconium, from group 8, preferably Fe, from group 15, preferably antimony, from group 13, preferably aluminium, boron, thallium and metals from group 14, preferably germanium.

These promoters are very largely present in homogenious form, i.e. with relatively little formation of domains. The incorporated promoters "M" are generally present in the organic/inorganic hybrid materials in disperse form and are advantageously attached via element-O—Si bonds. The chemical composition of these materials may vary over wide ranges. The proportion of the promoter element relative to silicon oxide is in the range from 0–10 mol %, preferably from 0–4 mol %. Two or more different promoters may, of course, also be used. The promoters are preferably used in the form of promoter precursor compounds soluble in the particular solvent, such as promoter salts and/or organo-promoter compounds and/or organic/inorganic promoter compounds.

The promoters may increase both the catalytic activity of the composition and the service life of the composition in catalytic hydrocarbon oxidation reactions.

When in the desiccated state, the compositions according to the invention containing gold and/or silver particles and materials containing Ti may be described in approximate terms by the following empirical formula (I) (without taking account of the residues formed on the surface after modification and possibly incompletely reacted groups):

$$SiO_x * TiO_y * MO_z * E \tag{I}$$

$SiO_x$ and $TiO_y$ denote not only silicon oxide and titanium oxide, but also true mixed oxides between the elements silicon and titanium. M is a promoter, preferably Ta, Fe, Sb, V, Nb, Zr, Al, B, Tl, Y, Ge or combinations thereof, E means gold and/or silver (noble metal) and x, y and z denote the number of oxygens actually required to saturate the valences of Si, Ti and M.

The composition (I) described above may be varied over wide ranges.

Relative to silicon oxide, the proportion of titanium oxide is between 0.1 and 10 mol %, preferably between 0.5 and 8.0 mol %, particularly preferably between 1.0 and 5.0 mol %. The proportion of $MO_z$, relative to silicon oxide, is between 0 and 12 mol %. The proportion of E, relative to the noble metal-free composition, is between 0.001 and 15 wt. %. In the case of gold, this proportion is preferably between 0.001 and 2 wt. %, in the case of silver preferably between 0.01 and 15 wt. %.

The noble metals may be applied in the form of precursor compounds, such as salts or organic complexes or compounds, onto the materials containing titanium in known manner, for example by precipitation, solution impregnation, incipient wetness, sputtering, colloids, CVD.

The compositions according to the invention are surface-modified in order to achieve long catalyst service lives.

Surface modification may proceed both before and after coating with the noble metal.

For the purposes of the invention, modification is in particular taken to mean the application of groups selected from among alkylsilicon, arylsilicon, alkyl groups containing fluorine or aryl groups containing fluorine onto the surface of the supported composition, wherein the groups are attached to the functional groups (for example OH groups) on the surface by a covalent or coordinate bond. However, any other surface modification is explicitly included within the scope of the present invention.

Modification is preferably performed with organosilicon and/or organosilicon or organic compounds containing fluorine, wherein organosilicon compounds are preferred.

Organosilicon compounds (alkylsilicon, arylsilicon etc.) which may be considered include any silylating agents known to the person skilled in the art, such as organic silanes, organic silylamines, organic silylamides and the derivatives thereof, organic silazanes, organic siloxanes and other organosilicon compounds, which may, of course, also be used in combination. Organosilicon compounds also explicitly subsume compounds prepared from silicon and partially fluorinated or perfluorinated organic residues.

Alkyl is taken to mean any linear or branched alkyl residues having 1 to 50 C atoms known to the person skilled in the art, such as methyl, ethyl, n-propyl, i-propyl, n-butyl, i-butyl, t-butyl, n-pentyl, i-pentyl, neopentyl, hexyl and further homologues, which for clarity's sake need not be listed here, which residues may in turn themselves be substituted. Substituents which may be considered in this connection are halogen, nitro, or also alkyl or alkoxy, as well as cycloalkyl or aryl, such as benzoyl, trimethylphenyl, ethylphenyl, chloromethyl, chloroethyl and nitromethyl. The term alkyl here explicitly also subsumes cycloalkyls and alkylaryls, such as cyclohexane, benzyl, vinylbenzyl, benzoyl. Methyl, ethyl, n-propyl, i-propyl, n-butyl, i-butyl, t-butyl and benzoyl are preferred. In the stated alkyl residues, individual, two or more or also all the C atoms may be replaced by Si atoms, O atoms or S atoms, wherein siloxanes may be mentioned by way of example.

Aryl is taken to mean any mono- or polycyclic aryl residues having 6 to 14 C atoms known to the person skilled in the art, such as phenyl, naphthyl, fluorenyl, which may in turn themselves be substituted. Substituents which may be considered in this connection are halogen, nitro, hydroxyl or also the stated alkyl or aryl residues, such as bromophenyl, chlorophenyl, toloyl and nitrophenyl.

Methyl, ethyl, propyl, t-butyl, methoxy, ethoxy, cyclohexyl, benzoyl, methoxy, ethoxy, phenyl, naphthyl, chlorophenyl, toloyl and nitrophenyl are preferred.

The person skilled in the art takes halogen to mean fluorine, chlorine, bromine or iodine, with fluorine, chlorine and bromine being preferred.

Specific examples of organic silanes are trialkylsilanes, dihalodialkylsilanes, nitrotrialkylsilanes, halotrialkylsilanes, halodialkylarylsilanes, dialkoxyalkylhalosilanes. alkylarylhalosilanes, trialkoxyhalosilanes, dialkylarylhalosilanies, alkyldiarylsilanes, aryldialkylsilanes, diarylsilanes, triarylsilanes and perfluorinated alkyl- or arylalkoxysilanes.

Specific examples of organic silylamines are N-trialkylsilylimidazoles, N-trialkylsilylimidazoles, N-trialkylsilyldialkylamines, N-trialkylsilylpyrroles, N-trialkylsilylpyrrolidines, N-trialkylsilylpiperidines and pentafluorophenyldialkylsilylamines.

Specific examples of organic silylamides and the derivatives thereof are N,O-bistrialkylsilylacetamides, N,O-bistrialkylsilyltrihaloacetamides, N-trialkylsilylacetamides, N-alkyl-N-trialkylsilylacetamides, N-alkyl-N-trialkylsilyltrihaloacetamides and N-alkyl-N-trialkylsilylperhaloalkylamides.

Specific examples of organic silazanes are hexaalkyldisilazanes, heptaalkyldisilazanes, 1,1,3,3-tetraalkyldisilazanes, 1,3-bis(haloalkyl) tetraalkyldisilazanes, 1,3-diaryl-1,1,3,3-tetraalkyldisilazanes and 1,3-diaryltetraalkyldisilazanes. Examples of other compounds containing silicon are N-alkoxy-N,O-bistrialkylsilyltrihaloacetamides, N-alkoxy-N,O-bistrialkylsilyl carbamates, N,O-bistrialkylsilyl sulfamates, trialkylsilyltrifluoromethane sulfonate and N,N'-bistrimethylsilylurea.

Preferred alkylsilicon residues are hexamethyldisilane, hexamethyldisiloxane, hexamethyldisilazane and N-methyl-N-trimethylsilyltrifluoroacetamide.

Alkylene and arylene containing fluorine are taken to mean any described alkyl and aryl residues which bear at least one fluoro substituent, in particular alkyl or aryl residues having one, two, three, four, five, six, seven, eight and nine fluoro substituents or perfluorinated alkyl and aryl residues. Hexafluoro-2-methylisopropanol, 1-chloro-3-fluoroisopropanol, 3-chloro-4-fluorobenzoyl chloride, 2-chloro-4-fluorobenzoic acid, chloro- and bromopentafluoroethane, bromoperfluoroheptane, hexafluoroglutaric acid or pentafluorobenzoyl chloride or perfluorooctyltrietlioxysilane are particularly preferably used.

Preferably more than 10%, in particular more than 50%, very particularly preferably more than 80% of the functional groups on the surface (for example OH groups) of the supported composition are coated with the alkylsilicon, arylsilicon, alkyl groups containing fluorine or aryl groups containing fluorine.

The polarity of the surface of the supported composition according to the invention is purposefully established by hydrophobic coating of the surface.

Although the morphology and particle size of the supported composition according to the invention may apparently be varied over wide ranges, we have found that it is particularly favourable to use homogeneous mixed oxides having elevated surface areas of >20 $m^2/g$, preferably of >50 $m^2/g$. This supported composition is characterised by its chemical flexibility in the chemical composition, such as the nature of the metal, metal content and alkyl content, and the purposeful control exerted on catalyst activity, selectivity and service life by treating the surface in order to prevent deactivation/blocking.

The stated objects are furthermore achieved by a process for the production of a supported composition containing gold and/or silver particles, titanium oxide and a support containing silicon, characterised in that the surface of the support containing silicon and/or the supported composition is treated.

For the purposes of the invention, treatment is in particular taken to mean application of groups selected from among alkylsilicon, arylsilicon, alkyl groups containing fluorine or aryl groups containing fluorine onto the surface of the supported composition, wherein the groups are attached to the functional groups (for example OH groups) on the surface by a covalent or coordinate bond. However, any other surface modification is explicitly included within the scope of the present invention.

Treatment is preferably performed with organosilicon compounds and/or organosilicon or organic compounds containing fluorine, wherein organosilicon compounds are preferred.

Organosilicon compounds which may be considered are any silylating agents known to the person skilled in the art, such as organic silanes, organic silylamines, organic silylamides and the derivatives thereof, organic silazanes, organic siloxanes and other organosilicon compounds, which may, of course, also be used in combination. Organosilicon compounds also explicitly subsume compounds of silicon and partially fluorinated or perfluorinated organic residues.

Specific examples of organic silanes are chlorotrimethylsilane, dichlorodimethylsilane, chlorobromodimethylsilane, nitrotrimethylsilane, chlorotrimethylsilane, iododimethylbutylsilane, chlorodimethylphenylsilane, chlorodimethylsilane, dimethyl-n-propylchlorosilane, dimethylisopropylchlorosilane, t-butyldimethylchlorosilane, tripropylchlorosilane, dimethyloctylchlorosilane, tributylchlorosilane, trihexylchlorosilane, dimethylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, methylphenylchlorosilane, triethoxychlorosilane, dimethylphenylchlorosilane, methylphenylvinylchlorosilane, benzyldimethylchlorosilane, diphenylchlorosilane, diphenylmethylchlorosilane, diphenylvinylchlorosilane, tribenzylchlorosilane and 3-cyanopropyldimethylchlorosilane.

Specific examples of organic silylamines are N-trimethylsilyldiethylamine, pentafluorophenyldimethylsilylamine, including N-trimethylsilylimidazoles, N-t-butyldimethylsilylimidazole, N-dimethylethylsilylimidazole, N-dimethyl-n-propylsilylimidazole, N-dimethylisopropylsilylimidazole, N-trimethylsilyldimethylamine, N-trimetliylsilylpyrrole, N-trimethylsilylpyrrolidine, N-trimethylsilylpiperidine and 1-cyanoethyl(diethylamino)dimethylsilane.

Specific examples of organic silylamides and the derivatives thereof are N,O-bistrimethylsilylacetamide, N,O-bistrimethylsilyltrifluoroacetamide, N-trimethylsilylacetamide, N-methyl-N-trimethylsilylacetamide, N-methyl-N-trimethylsilyltrifluoroacetamide, N-methyl-N-trimethylsilylheptafluorobutyramide, N-(t-butyldimethylsilyl)-N-trifluoroacetamide and N,O-bis(diethylhydrosilyl)trifluoroacetamide.

Specific examples of organic silazanes are hexamethyldisilazane, heptamethyldisilazane, 1,1,3,3-tetramethyldisilazane, 1,3-bis(chloromethyl)tetramethyldisilazane, 1,3-divinyl-1,1,3,3-tetramethyldisilazane and 1,3-diphenyltetramethyldisilazane.

Examples of other organosilicon compounds are N-methoxy-N,O-bistrimethylsilyltrifluoroacetamide, N-methoxy-N,O-bistrimethylsilyl carbamate, N,O-bistrimethylsilyl sulfamate, trimethylsilyltrifluoromethane sulfonate and N,N'-bistrimethylsilylurea.

Examples of fluorinated organosilicon compounds are perfluorooctyltriethoxysilane, perfluoropentyltriethoxysilane or perfluoropentyltributoxysilane.

Preferred silylating reagents are hexamethyldisilazane, hexamethyldisiloxane, N-methyl-N-(trimethylsilyl)-2,2,2-trifluoroacetamide MSTFA and trimethylchlorosilane.

The catalysts may also be subjected to water treatment before silylation in order to increase surface OH groups. Water treatment means in this connection that, prior to the silylating process step, the catalyst is brought into contact with liquid water or an aqueous saturated ammonium chloride solution and/or ammonium nitrate solution, or ion exchange with polyvalent cations (aqueous solutions of, for example, $Ca^{2+}$ or $La^{3+}$), for example the catalyst is suspended in the treatment medium and then dried (for example at 300° C.), or the catalyst is treated with steam at >100° C., preferably at 150–450° C., for 1–6 hours. The catalyst is particularly preferably treated with steam at 200–450° C. for 2–5 hours. Excess water is then removed. Water or the aqueous salt solutions used may also be applied onto the catalyst support by spray impregnation. Spray impregnation is in particular preferred with moulded support materials.

Organic compounds containing fluorine which may be considered are any alkyl and aryl residues known to the person skilled in the art which bear at least one fluoro substituent, in particular alkyl or aryl residues having one, two, three, four, five, six, seven, eight and nine fluoro substituents or perfluorinated alkyl and aryl residues. Hexafluoro-2-methylisopropanol, 1-chloro-3-fluoroisopropanol, 3-chloro-4-fluorobenzoyl chloride, 2-chloro-4-fluorobenzoic acid, chloro- and bromopentafluoroethane, bromoperfluoroheptane, hexafluoroglutaric acid or pentafluorobenzoyl chloride are particularly preferably used.

There are no limitations to the sequence of treatment of the supported composition according to the invention.

Preparation may proceed by applying titanium oxide on silicon oxide with subsequent application of gold and/or silver and surface treatment, or titanium and gold and/or silver centres may simultaneously be applied onto supports containing silicon and the surface treated, or titanium, gold and silicon components are simultaneously reacted in a copolycondensation reaction and the surface treated, or titanium and silicon components are simultaneously reacted in a copolycondensation reaction, coated with gold and the surface treated or titanium centres are chemically bonded to the silicon dioxide, the surface treated and subsequently coated with gold and/or silver.

The titanium oxide may be produced in situ on support materials containing silicon from titanium precursor compounds, for example by saturation from supernatant solution (impregnation) and/or be applied with a quantity of solvent corresponding to the absorption capacity of the support (incipient wetness), precipitation (deposition precipitation), vapour deposition, and by sol/gel methods and equally well by colloid methods, sputtering or vapour condensation. In the case of saturation, titanium precursor compounds capable of reacting with the surface silanol groups are advantageously used.

Titanium oxide is also produced in situ by grafting with titanocene chloride on supports containing silicon, possibly in the presence of a base. In this case, the ($\eta_5$—$C_5H_2)_2TiCl_2$ reacts with terminal surface silanol groups. After grafting, drying and calcination, (≡SiO)$_3$TiOH complexes probably form the dominant titanium species. The support materials containing titanium are coated with gold and/or silver in the next step.

Suitable titanium precursor compounds as catalytic titanium species are known from the prior art, such as soluble titanium salts (for example titanium halides, nitrates, sulfates, titanium salts of inorganic or organic acids and titanic acid esters).

Titanium derivatives such as tetraalkyl titanates with $C_1$-$C_6$ alkyl groups such as methyl, ethyl, n-propyl, n-butyl, isobutyl, tert.-butyl etc. or other organic titanium species such as titanyl acetylacetonate, dicyclopentadienyltitanium dichloride are preferably used. Tetra-n-butylorthotitanate, titanium acetylacetonate, titanocene dichloride and titanium tetrachloride are preferred titanium precursor compounds.

—Si—O—Ti— groups are also advantageously generated by simultaneous polymerisation of suitable Si and Ti precursors, for example copolycondensation reactions to yield amorphous xerogels or xerogels, or by hydrothermal synthesis to yield crystalline mixed oxide zeolites, silicalites or the like. The sol/gel process is based on the polycondensation of hydrolysed, colloidally dissolved metal component mixtures (sol) to form an amorphous, three-dimensional network (gel). The following reaction scheme is intended to clarify the process:

ferred by silicon. These centres are probably the mentioned catalytically active centres (site-isolated centres).

We have found that selectivity and, especially, activity may be increased in the described heterogeneous catalysis it the catalytically active metal centres are incorporated into a defined pore architecture. In this manner, secondary reactions may be suppressed. Once coated with noble metal (gold and/or silver), $SiO_x/TiO_y$ mixed oxides which have been produced by a homogeneous copolycondensation reaction thus comprise highly active, selective oxidation catalysts. After surface treatment, such systems exhibit industrially useful catalyst service lives of many months and more, combined with excellent selectivities.

We have surprisingly also found that sol/gel based catalyst systems (base or acid catalysed hydrolysis, condensation and gelation (copolycondensation) of suitable silicon, titanium and additional promoter precursors, both with and without template compounds) comprise, after surface treatment, highly selective and active oxidation catalysts. The foreign oxides of titanium and the already described promoters which are incorporated into the silicon dioxide lattice are very largely present in homogeneous form, i.e. with little formation of domains. The incorporated elements are present in the amorphous mixed oxides in highly disperse form and are largely attached to the inorganic polymer via element-O—Si bonds. The chemical composition of these amorphous mixed oxides may be varied over wide ranges during production in the sol/gel process. The catalysts obtained in this manner are particularly preferably brought into contact with organic silylation reagents before

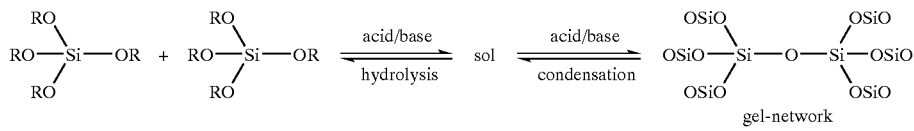

Suitable precursor compounds of the corresponding support materials are, for example, alkoxides of silicon and/or titanium. Typical molar $H_2O$:hydrolysable Si(Ti) species ratios are, for example, 0.5–32, preferably 0.5–3. Suitable catalyst support materials, such as pyrogenic silicas, Aerosils or Cab-o-sils may be suspended or dispersed in the colloidal silica sols. Additional condensable, multifunctional molecules, such as for example monomeric or polymeric glycols, metal chlorides or similar compounds may also be used for purposeful "material design". Like the hydrolysed alkoxymetallates, these polymers may be homogeneously incorporated into the gel network. Adding hydrophobic organic solvents to the sol phase (dispersed phase), for example monofunctional aliphatic alcohols having more than eight carbon atoms, brings about the formation of an emulsion (dispersed sol phase and homogeneous emulsion liquid) and thus provides the opportunity for further tailoring of the material.

Gels of virtually all metal, semi-metal or non-metal oxides are known and many of them are suitable for the production of xerogels and aerogels. The sol/gel process makes it possible to prepare, inter alia, extremely homogeneous $SiO_x/TiO_y$ mixed oxides. At elevated titanium contents (>15 wt. %), domains are formed due to the preferred Ti—O—Ti homocondensation reaction, in which the octahedral Ti coordination known from pure $TiO_2$ prevails. In the case of dilute systems, "$TiO_y$ in $SiO_x$" (<7 wt. % Ti), a homogeneous, i.e. domain-free, Ti distribution occurs, wherein the Ti also assumes the fourfold coordination prethe oxidation reaction. These amorphous or, after hydrothermal synthesis, crystallised mixed oxides produced on the basis of $SiO_x$ are excellent, highly selective redox catalysts.

After application of gold and/or silver and surface treatment, the sol/gel process yields the micro- or macroporous supported compositions according to the invention.

The desired surface polarity may, however, be established not only by bringing the supported compositions into contact with organic silylation reagents, but also advantageously by hydrolysis of, for example, alkyl(aryl)silanes and/or alkyl (aryl)silanes containing fluorine of the type $RSi(OR')_3$, or of the type $RTi(OR')_3$, to yield alkyl(aryl)-modified silica gels or silica gels containing titanium. The hydrophobic or lipophilic properties in the pores and on the surface of the silica gel particles may be adjusted by selecting the alkyl, alkylene or aryl residue R on the silicon. Silica gels of this type are suitable matrices for metal catalysts.

Copolycondensation of suitable silicon, titanium and promoter species is another preferred method for the production of the supported compositions according to the invention. Suitable Si, Ti and promoter species are in principle any appropriate compounds known to the person skilled in the art which may serve as precursors for the corresponding oxides or hydroxides. Polycondensation may here proceed in aqueous systems or in organic systems.

Apart from silica gels, silica sols and water glasses, suitable silicon species which are used are tetraalkyl orthosilicates, such as tetramethyl orthosilicate, tetraethyl orthosilicate. Surface polarity is purposefully adjusted by advantageously partially or entirely substituting proportions of tetraalkyl orthosilicates by trialkoxysilicon species such as for example trialkoxymethylsilane and/or trialkoxyphenylsilane and/or trialkoxychlorosilane. Apart from monomeric alkoxides, polymeric systems, such as for example poly(diethoxysilane), poly(diethoxysilane s-butylaluminate) etc. may equally well be used.

In an analogous manner, titanium salts (for example titanium halides, nitrates, sulfates, ammonium hexafluorotitanate) are preferably used as suitable titanium species. Titanium derivatives such as tetraalkyl titanates with $C_1$–$C_6$ alkyl groups such as methyl, ethyl, n-propyl, n-butyl, isobutyl, tert.-butyl, or other organic titanium species such as titanyl acetylacetonate, dicyclopentadienyltitanium dichloride are also preferably used. Tetra-n-butyl orthotitanate is another preferred titanium component. If small quantities of tetraalkyl orthotitanate are substituted by trialkoxytitanium species, for example trialkoxyphenyltitanium, surface polarity may additionally be adjusted. Apart from monomeric alkoxides, polymeric systems, such as for example poly(diethoxysiloxane/ethyl titanate), poly(octyleneglycol titanate) etc. may equally well be used.

Similarly, any promoter derivatives suitable as precursors or sources of promoter oxides, in particular tantalum oxide, antimony oxide, iron oxide and aluminium oxide, are also suitable. Although any salts, such as for example halides, nitrates and hydroxides may be used, the alkoxides, for example ethoxide, propoxide, etc., of these metals are preferred.

Coprecipitation products or co-gels of Si, Ti and promoter, Si and Ti, Si and promoter, Ti and promoter or Si and promoter may also be used as starter reagents.

Products produced by a process based on water glass (an aqueous sodium silicate solution is hydrolysed under acidic conditions for example after ion exchange) or processes in which the silicic acid is transferred into an organic solvent and then condensed in this medium with acidic, neutral or basic catalysis are particularly suitable, especially for large scale industrial applications.

The said products (water glasses) are further preferred starting materials for the purposes of the invention.

We have surprisingly found that, for the catalytic oxidation of alkanes and alkenes, the supported compositions have a catalytic activity and service life several orders of magnitude greater than those of hitherto known catalyst systems.

Using the supported compositions according to the invention for oxidising hydrocarbons is thus another way of achieving the stated object and is also provided by the present invention.

Use according to the invention may, in principle, be applied to any hydrocarbons. The term hydrocarbon is taken to mean unsaturated or saturated hydrocarbons such as olefins or alkanes, which may also contain heteroatoms, such as N, O, P, S or halogens. The organic component to be oxidised may be acyclic, monocyclic, bicyclic or polycyclic and may be monoolefinic, diolefinic or polyolefinic. In the case of organic components having two or more double bonds, the double bonds may be present in conjugated and unconjugated form. The hydrocarbons oxidised are preferred those from which such oxidation products are formed which have a sufficiently low partial pressure to allow continuous removal of the product from the catalyst. Unsaturated and saturated hydrocarbons having 2 to 20, preferably 2 to 10 carbon atoms are preferred, in particular ethene, ethane, propene, propane, isobutane, isobutylene, 1-butene, 2-butene, cis-2-butene, trans-2-butene, 1,3-butadiene, pentene, pentane, 1-hexene, 1-hexane, hexadienes, cyclohexene, benzene.

The supported compositions may here be used for oxidation reactions in any desired physical form, for example ground powders, spherical particles, pellets, extrudates, granules, etc.

A preferred use is the gas phase reaction of oxygen with hydrogen in the presence of the supported compositions according to the invention. This use selectively yields epoxides from olefins, ketones from saturated secondary hydrocarbons and alcohols from saturated tertiary hydrocarbons. Depending upon the educt used, catalyst service lives amount to many months or more.

The relative molar ratio of hydrocarbon, oxygen, hydrogen and optionally a diluent gas may be varied within wide ranges.

The molar ratio of the introduced hydrocarbon relative to the total number of moles of hydrocarbon, oxygen, hydrogen and diluent gas may be varied within wide ranges. Hydrocarbon is preferably used in an excess, relative to introduced oxygen (on a molar basis). Hydrocarbon content is typically greater than 1 mol % and less than 60 mol %. Hydrocarbon contents used are preferably in the range from 5–35 mol %, particularly preferably from 10–30 mol. %. As hydrocarbon contents rise, productivity is increased and hydrogen combustion reduced.

Oxygen may be used in the most varied form, for example molecular oxygen, air and nitrogen oxide. Molecular oxygen is preferred. The molar oxygen content, relative to the total number of moles of hydrocarbon, oxygen, hydrogen and diluent gas, may be varied within wide ranges. Oxygen is preferably used in a molar deficit relative to the hydrocarbon. Oxygen is preferably used in the range from 1–6 mol %, particularly preferably from 6–15 mol %. As oxygen contents rise, productivity is increased. An oxygen content of less than 20 mol % should be selected on safety grounds.

In the absence of hydrogen, the supported compositions according to the invention exhibit only very low activity and selectivity. At temperatures of up to 180° C., productivity is very low in the absence of hydrogen, while at temperatures of greater than 200° C., large quantities of carbon dioxide are formed together with partial oxidation products. Any known hydrogen source may be used, such as for example molecular hydrogen from dehydrogenation of hydrocarbons and alcohols. In another embodiment of the invention, the hydrogen may also be produced in situ in an upstream reactor, for example by dehydrogenating propane or isobutane or alcohols, such as for example isobutanol. Hydrogen may also be introduced into the reaction system as a complexed species, for example catalyst/hydrogen complex. The molar hydrogen content, relative to the total number of moles of hydrocarbon, oxygen, hydrogen and diluent gas, may be varied within wide ranges. Typical hydrogen contents are greater than 0.1 mol %, preferably 5–80 mol %, particularly preferably 10–65 mol %. As hydrogen contents rise, productivity is increased.

In addition to the essentially required educt gases described above, it is optionally also possible to use a diluent gas, such as nitrogen, helium, argon, methane, carbon dioxide or similar gases which behave inertly. Mixtures of the described inert components may also be used. Addition of inert components is favourable for dissipating the heat liberated in this exothermic oxidation reaction and from the standpoint of safety. If the process according to the invention is performed in the gas phase, gaseous diluent components are preferably used, such as for example nitrogen, helium, argon, methane and possibly steam and carbon dioxide. While steam and carbon dioxide are indeed not entirely inert, they have a positive effect at very low concentrations (<2 vol. %). When the invention is performed in the liquid phase, an oxidation-resistant and thermally stable inert liquid is conveniently selected (for example alcohols, polyalcohols, polyethers, halogenated hydrocarbons).

The supported compositions according to the invention are also suitable in the liquid phase for the oxidation of hydrocarbons. Both in the presence of organic hydroperoxides (R—OOH), liquid phase olefins are highly selectively converted into epoxides on the described catalysts, and in the presence of oxygen and hydrogen, liquid phase olefins are highly selectively converted into epoxides on the described catalysts.

We have found that the selective oxidation reaction described above is highly sensitive to catalyst structure. When nanodisperse gold and/or silver particles are present in the supported composition, an increase in productivity of the selective oxidation product was observed.

The spatially close interaction of gold and/or silver with titanium oxide (perimetric interface) is particularly effective, i.e. excellent epoxidation catalysts in the presence of oxygen and hydrogen are obtained when amorphous or crystalline mixed oxide support materials containing titanium, for example $SiO_x/TiO_y$, mixed oxides, are used. The activity of the gold/titanium dioxide/silicon dioxide catalysts and catalyst service life may be further increased by incorporating small quantities of promoters, for example foreign metals, especially by incorporating tantalum and/or iron and/or antimony and/or aluminium. Surface treatment according to the invention ultimately brings about industrially useful catalyst service lives of many months. These mixed oxides may be produced on an industrial scale without processing problems and at favourable cost.

The characteristic features of the present invention are illustrated in the following Examples by means of catalyst preparations and a catalytic test reaction.

The invention is, of course, not limited to the following Examples.

EXAMPLES

Catalyst Testing Protocol (Test Protocol)

A metal tubular reactor of an internal diameter of 10 mm and length of 20 cm was used, the temperature of which was controlled by means of a temperature-controlled oil bath. The reactor was supplied with educt gases with a set of four mass flow controllers (hydrocarbon, oxygen, hydrogen, nitrogen). 0.5 g of pulverulent catalyst were initially introduced for the reaction at 150° C. and 3 bar overpressure. The educt gases were metered into the reactor from the top. Standard catalyst loading was 4 l/g cat./h. Propene was selected by way of example as the "standard hydrocarbon". The oxidation reactions were performed using a stream of gas having an increased nitrogen content, hereinafter always referred to as the standard gas composition: $N_2/H_2/O_2/C_3H_6$=15/63/10/12%. The reaction gases were quantitatively analysed by gas chromatography. The individual reaction products were separated by gas chromatography using a combined FID/TCD method in which the gases passed through three capillary columns:

FID: HP-Innowax, 0.32 mm internal diameter, 60 m long, 0.25 µm film thickness

TCD: Columns connected in series HP-Plot Q, 0.32 mm internal diameter, 30 m long, 20 µm film thickness HP-Plot Molsieve 5A, 0.32 mm internal diameter, 30 m long, 12 µm film thickness.

Example 1

This Example describes the preparation of an amorphous catalyst support consisting of oxides of silicon and titanium which is coated with gold particles and then surface-modified.

26 g of tetraethoxysilane (120 mmol) (TEOS, Acros, 98%) were placed in 22.5 ml of i-propanol, mixed together, combined with 2.25 g of 0.1 N HCl and stirred for 2 hours. 1.06 g of tetrabutoxytitanium (3.1 mmol) (Acros, 98%) were added dropwise to this solution and stirred for 15 minutes. The homogeneous batch was combined with 23 ml of 2% aqueous $NH_3$ solution. The batch reached the gel point after approx. 5 minutes, was left to stand for 10 hours and dried at 120° C., initially for 1 hour at standard pressure, then for approx. 20 hours under a vacuum (50 mbar) and calcined at 300° C. for 3 hours.

2.5 g of the material was initially introduced with 0.5 g of 1,1,1,3,3,3-hexamethyldisilazane (3 mmol) (Merck) into dry hexane with stirring, stirred for 2 hours at 60° C., the solids were filtered out, washed with 50 ml of hexane and dried for 5 hours at 120° C. under a vacuum. Surface modification by silylation was repeated.

4 g of the support containing titanium were initially introduced into 35 ml of methanol, combined with 70 mg of $HAuCl_4$ (0.178 mmol) (Merck) in 5 ml of methanol, adjusted to pH 8 with 1.1 ml of 2 N $K_2CO_3$, stirred for 30 minutes, 4 ml of monosodium citrate solution were added, the pH readjusted to pH 8 with 2 N $K_2CO_3$ and the mixture stirred for 120 minutes. The solids were then separated, washed 3 times with 40 ml portions of water, dried for 10 hours at 120° C. at standard pressure and calcined for 3 hours at 350° C. The gold content of the gold/titanium/silicon catalyst was 0.52 wt. % (ICP analysis).

On testing in accordance with the test protocol, steady-state propene conversions of 1.5% were achieved over 300 hours at constant PO selectivities of 94%.

Example 2

This Example describes the preparation of an amorphous catalyst support consisting of the oxides of silicon, titanium and tantalum, which was surface-modified and then coated with gold. Catalyst preparation proceeds in a similar manner to Example 1, but 60 minutes after the addition of tetrabutoxytitanium, the homogeneous batch was combined with 765 mg (1.86 mmol) of $Ta(OEt)_5$ (Chempur), stirred for 15 minutes and gelled, worked up and modified in a similar manner to Example 1.

On testing in accordance with the test protocol, steady-state propene conversions of 2.2% were achieved over 300 hours at constant PO selectivities of 94%.

Example 3

This Example describes the preparation of an amorphous catalyst support consisting of the oxides of silicon, titanium and tantalum, which was surface-modified and then coated with gold. Catalyst preparation proceeds in a similar manner to Example 2, but the gold coated catalyst support is treated with steam at 300° C. for 3 hours before silylation, then dried at 300° C. for 2 hours and finally silylated in a similar manner to Example 1.

On testing in accordance with the test protocol, steady-state propene conversions of 2.4% were achieved over 200 hours at constant PO selectivities of 94%.

Example 4

This Example describes the preparation of a hydrophobic, amorphous catalyst support consisting of the oxides of silicon and titanium, which is coated with gold particles and then surface-modified. Catalyst preparation proceeded in similar manner to Example 1, but 5 mol % of TEOS were replaced with triethoxymethylsilane (Merck). A uniform calcination temperature of 230° C. was selected.

On testing in accordance with the test protocol, steady-state propene conversions of 1.9% were achieved over 300 hours at constant PO selectivities of 94%.

Example 5

This Example describes the preparation of a catalyst support consisting of the oxides of silicon and titanium, which was surface-modified and then coated with gold. The catalyst support containing Si and Ti is obtained by impregnating silica with titanocene dichloride.

20 g of Aerosil 380 (Degussa) are suspended in 150 ml of saturated ammonium chloride solution, stirred for 3 hours at 50° C., filtered out, washed 3 times with 50 ml portions of water, dried for 3 hours at 120° C. and calcined for 3 hours at 300° C.

1568 mg of titanocene dichloride (Merck) were dissolved in 300 ml of chloroform, 10 g of dry Aerosil 380 (Degussa, pyrogenic silicon dioxide, 380 m$^2$/g) were added, the mixture stirred for 30 minutes, 1867 mg of triethylamine were added, the mixture stirred for 120 minutes, vacuum filtered and washed with 50 ml of chloroform, dried for 3 hours under nitrogen at 120° C. and then calcined for 3 hours at 300° C. and for 1 hour at 500° C.

2 g of support containing titanium were initially introduced into 20 ml of hexane, 0.4 g of hexamethyldisilazane were added, the mixture stirred for 120 minutes at 60° C., separated and dried at 120° C. for 10 hours.

64 ml of methanolic tetrachloroauric acid solution (1.25 g of Au/l) were initially introduced, 4 g of the material containing titanium added, adjusted to pH 8 with 1.0 ml of $K_2CO_3$ (2 N), stirred for 30 minutes, 4 ml of monosodium citrate solution were added, the pH readjusted to pH 8 with 2 N $K_2CO_3$, the mixture stirred for 120 minutes, the solids were separated, washed 3 times with 40 ml portions of $H_2O$, dried for 2 hours at 150° C. and calcined for 5 hours at 350° C.

On testing in accordance with the test protocol, steady-state propene conversions of 2.1% were achieved over 300 hours at constant PO selectivities of 93%.

Example 6

This Example describes the preparation of a catalyst support consisting of the oxides of silicon and titanium which was surface-modified and then coated with gold. The catalyst support containing Si and Ti was obtained by impregnating silica with tetraisopropoxytitanium.

70 g of Aerosil 380 were treated with ammonium chloride solution in a similar manner to Example 5.50 g of Aerosil 380 (Degussa, pyrogenic silicon dioxide, 380 m$^2$/g), 2.2 g of tetraisopropoxytitanium (7.7 mmol) (Merck), 1.6 g of acetylacetonate and 200 ml of dry isopropanol were initially introduced with stirring, homogenised for 30 minutes, the solids filtered out, resuspended in 50 ml of isopropanol for washing, stirred for 10 minutes and refiltered. This washing process was repeated. The solids were dried at 120° C. under nitrogen and calcined for 3 hours at 300° C. and for 1 hour at 500° C.

2 g of the material containing titanium were initially introduced into 20 ml of hexane, 0.2 g (1.2 mmol) of hexamethyldisilazane were added, the mixture stirred for 120 minutes at 60° C., separated and dried for 10 hours at 120° C.

70 ml of methanolic tetrachloroauric acid solution (0.7 g of Au/l) were initially introduced, 5 g of the material containing titanium added, the pH adjusted to 8 with 1.0 ml of $K_2CO_3$ (2 N), the mixture stirred for 30 minutes, 2 ml of monosodium citrate solution were added, the pH readjusted to pH 8 with 2 N $K_2CO_3$, the mixture stirred for 120 minutes, the solids were separated, washed 4 times with 20 ml portions of $H_2O$, dried for 2 hours at 150° C. and calcined for 3 hours at 350° C. The catalyst contained 0.6 wt. % of gold (ICP).

On testing in accordance with the test protocol, steady-state propene conversions of 1.8% were achieved over 300 hours at constant PO selectivities of 93%.

Example 7

Comparative Example

This Example describes the preparation of a catalyst support consisting of the oxides of silicon and titanium, which was coated with gold particles. The catalyst support containing Si and Ti was obtained by impregnating silica with titanyl acetylacetonate.

30 g of Aerosil 200 (pyrogenic silicon dioxide, Degussa, 200 m$^2$/g) were suspended in 250 ml of dry methanol, combined with 0.98 g of titanyl acetylacetonate and stirred for 2 hours at room temperature. The suspension was evaporated to dryness in a rotary evaporator, the solid was then dried at 130° C. and calcined in a stream of air for 3 hours at 600° C.

0.16 g of tetrachloroauric acid were dissolved in 500 ml of distilled water, adjusted to phl 8.8 with a 2 N sodium hydroxide solution, heated to 70° C., combined with 10 g of the above silica containing titanium and stirred for 1 hour. In this manner, gold was immobilised in hydroxide form on the surface of the silica containing titanium. The solids were filtered out, washed with 30 ml of distilled water, dried for 10 hours at 120° C. and calcined in air for 3 hours at 400° C. According to ICP analysis, the catalyst contained 0.45 wt. % of gold.

On testing in accordance with the test protocol, at PO selectivities of 92%, a propene conversion of 2.3 mol % was achieved after 20 minutes, a propene conversion of 1.5 mol % after 100 minutes, a propene conversion of 1.0 mol % after 4 hours and a propene conversion of 0.5 mol % after 10 hours. Catalyst deactivation proceeded further over time.

Example 8

This Example describes the preparation of an amorphous catalyst support consisting of the oxides of silicon and titanium, which was surface-modified and then coated with gold. In contrast with Example 1, the catalyst support containing Si and Ti was obtained by acid catalysed copolycondensation.

9.15 g of TEOS (44 mmol, Merck) in 100 mmol of ethanol were combined with 0.65 g of tetraisopropoxytitanium (2.3 mmol) and 2 ml of 8 N HCl were apportioned dropwise. Hydrolysis, condensation and gelation were performed for 3 days in a closed polypropylene beaker. After 3 days' drying at room temperature, the gel was heated to 340 K at a heating rate of 0.1 K/min, kept at this temperature for 4 hours, heated at the same heating rate to 530 K and kept at that temperature for a further 5 hours for calcination. Cooling to room temperature was performed at 2 K/min.

2.5 g of the material containing titanium were initially introduced with 1 g of hexamethyldisilazane into dry hexane with stirring, stirred for 2 hours at 60° C., the solids filtered out, washed with 50 ml of hexane, dried at 120° C. under a vacuum.

40 ml of methanolic tetrachloroauric acid solution (0.70 g of Au/l) were initially introduced, 3 g of catalyst support containing titanium were added, the mixture adjusted to pH 8 with 1.0 ml of $K_2CO_3$ (2 N), stirred for 30 minutes, 2 ml of monosodium citrate solution were added, the pH value readjusted to pH 8 with 2 N $K_2CO_3$, the mixture stirred for 120 minutes, the solids were separated, washed 3 times with 20 ml portions of methanol, dried at 150° C. for 2 hours and calcined at 300° C. for 3 hours. The catalyst contained 0.6 wt. % of gold (ICP).

On testing in accordance with the test protocol, steady-state propene conversions of 1.5% were achieved over 100 hours at constant PO selectivities of 93%.

Example 9

This Example describes the preparation of a crystalline titanium silicalite catalyst support consisting of the oxides of silicon and titanium, which was surface-modified and then coated with gold. The catalyst support containing Si and Ti was obtained by hydrothermal synthesis.

275.5 g of TEOS (1.32 mol) (Merck) and 95.4 g of 0.05 N HCl were initially introduced under argon, stirred for 1 hour at room temperature, then cooled to 0° C., and 11.25 g (33 mmol) of tetrabutoxytitanium (Merck), dissolved in 66.2 g of isopropanol (Merck, analytical grade), were added dropwise over a period of 3 hours. The yellowish solution contained small quantities of solids, but these subsequently redissolved. Over a further 30 minutes, the batch was adjusted to room temperature (20° C.), 22 g of 20% tetra-propylammonium hydroxide solution (Sachen) were added dropwise over 3 minutes. The gel point was reached after 5 minutes. After standing for 10 hours, the communicated batch was transferred into a Teflon lined autoclave for hydrothermal synthesis for 24 hours at 170° C. The batch was washed 3 times with 30 ml of isopropanol, dried at 110° C. and slowly (10° C./min) heated under a stream of nitrogen to 560° C., kept at 560° C. under $N_2$ for 1 hour, then calcined in air for 10 hours at 560° C.

2.5 g of the calcined material were initially introduced with 1 g of hexamethyldisilazane in dry hexane with stirring, stirred for 2 hours at 60° C., the solids were filtered out, washed with 50 ml of hexane and dried at 120° C. under a vacuum.

40 ml of methanolic tetrachloroauric acid solution (0.70 g of Au/l) were initially introduced, 3 g of crystalline catalyst support containing titanium were added, the mixture adjusted to pH 8 with 1.0 ml of $K_2CO_3$ (2 N), stirred for 30 minutes, 2 ml of monosodium citrate solution were added, the pH value readjusted to pH 8 with 2 N $K_2CO_3$, the mixture stirred for 120 minutes, the solids were separated, washed 4 times with 20 ml portions of $H_2O$, dried at 150° C. for 2 hours and calcined at 350° C. for 3 hours. The catalyst contained 0.6 wt. % of gold (ICP).

On testing in accordance with the test protocol, steady-state propene conversions of 1.5% were achieved over 200 hours at constant PO selectivities of 93%.

Example 10

Trans-2-butene was selected as the unsaturated hydrocarbon instead of propene. An amorphous catalyst consisting of the oxides of silicon, titanium, tantalum and metallic gold was used for the partial oxidation of trans-2-butene. Catalyst preparation proceeded in a similar manner to Example 2.

On testing in accordance with the test protocol, steady-state trans-2-butene conversions of 2.0% were achieved over 100 hours at constant 2,3-epoxybutane selectivities of 91%.

Example 11

Cyclohexene was selected as the unsaturated hydrocarbon instead of propene. An amorphous catalyst consisting of the oxides of silicon, titanium, tantalum and metallic gold was used for the partial oxidation of cyclohexene. Catalyst preparation proceeded in a similar manner to Example 2.

On testing in accordance with the test protocol, steady-state cyclohexene conversions of 1.8% were achieved over 100 hours at cyclohexene oxide selectivities of 90%.

Example 12

1,3-Butadiene was selected as the unsaturated hydrocarbon instead of propene. An amorphous catalyst consisting of the oxides of silicon, titanium, tantalum and metallic gold was used for the partial oxidation of 1,3-butadiene. Catalyst preparation proceeded in a similar manner to Example 2.

On testing in accordance with the test protocol, steady-state butadiene conversions of 0.7% were achieved over 100 hours at butene oxide selectivities of 85%.

Example 13

This Example describes the preparation of an amorphous catalyst support consisting of the oxides of silicon, titanium and tantalum, which is coated with silver particles and then surface-modified. Catalyst support production proceeds in a similar manner to Example 2. The catalyst support is coated with silver particles instead of with gold.

10 g of catalyst support are added to the solution of 787 mg of silver nitrate (5 wt. % of silver relative to introduced support) in 100 ml of water at room temperature with stirring. The suspension is stirred for 1 hour at room temperature, the solids were separated and washed once with 20 ml of water. The moist solids are dried at 120° C. for 3 hours and then calcined in air at 250° C. for 2 hours and at 350° C. for 5 hours.

On testing in accordance with the test protocol, steady-state propene conversions of 0.4% were achieved over 50 hours at constant PO selectivities of 94%.

Investigation of Catalysts

Surface coating may be substantiated, for example, by so-called DRIFTS spectroscopy. DRIFTS (diffuse reflectance infrared Fourier transform spectroscopy) is a well established vibrational spectroscopy method for the structural characterisation of functional groups and adsorbates on the surfaces of solids. Details of the principle of the method and some sample applications from the area of heterogeneous catalysis may be found, for example, in the article by G. Mestl, H. Knözinger in *Handbook of Heterogeneous Catalysis*, volume 2, pages 539 et seq. (VCH, Weinheim, 1977) and the literature mentioned therein.

The catalyst materials according to the invention were characterised in the unsilylated and silylated state by storing appropriate samples for some hours at 200° C. in a drying cabinet, transferring them while hot into an inert gas cell and subjecting them to DRIFTS spectroscopic investigation without further contact with air (in order to avoid readsorption of $H_2O$ onto the sample surface).

FIG. 1 shows the DRIFTS spectrum of two silylated and unsilylated materials, which were produced according to Example 1. The silylation, performed with hexamethyldisilazane, resulted in virtually complete conversion of the terminal SiOH groups present on the surface of the unsilylated material and may be identified in the spectrum by the sharp band at 3740 cm$^{-1}$. The distinct bands around 3000 cm$^{-1}$ in the spectrum of the silylated material are attributable to the hydrocarbon coating (CH$_3$ groups) from the silylating agent. The unsilylated material also contains hydrocarbon residues, which possibly originate from the sol/gel process used to produce the support (these hydrocarbon residues were obviously not completely thermally decomposed by treating the material at a temperature of 200° C.).

What is claimed is:

1. A treated noble metal-containing catalyst comprising:
a noble metal-containing catalyst comprising (i) titanium oxide, (ii) a silicon support, (iii) gold and/or silver and, (iv) optionally, an oxide promoter, wherein the surface of the noble metal-containing catalyst is treated with a material having alkylsilicon, arylsilicon, alkyl groups containing fluorine or aryl groups containing fluorine thereby forming a treated noble metal-containing catalyst.

2. The catalyst according to claim 1, wherein at least 50% of the surface of the catalyst comprises alkylsilicon, arylsilicon, alkyl groups containing fluorine or aryl groups containing fluorine.

3. The catalyst according to claim 1, wherein at least 80% of the surface of the catalyst comprises alkylsilicon, arylsilicon, alkyl groups containing fluorine or aryl groups containing fluorine.

4. The catalyst according to claim 1, wherein the catalyst has an amorphous structure.

5. The catalyst according to claim 1, wherein about greater than 90% of the silicon support is silicon oxide.

6. The catalyst according to claim 1, wherein the silicon support has a surface area in the range of from about 25 to about 700 m$^2$/g.

7. The catalyst according to claim 1, wherein the silicon support is a silica gel, precipitated silica, precipitated silica gel, silicalite, and/or mixtures thereof.

8. The catalyst according to claim 1, wherein titanium oxide is present in an amount between about 1.0 and 5.0 mol %, based on the amount of silicon support.

9. The catalyst according to claim 1, wherein the concentration of gold is in the range of from about 0.005 to 1.5 wt. %, based on the total weight of the noble metal-containing catalyst.

10. The catalyst according to claim 1, wherein the concentration of silver applied is in the range of from about 0.1 to 10 wt. %, based on the total weight of the noble metal-containing catalyst.

11. The catalyst according to claim 1, wherein the gold has a diameter in the range of from about 0.5 to about 10 nm.

12. The catalyst according to claim 1, wherein the silver has a diameter in the range of from about 0.5 to about 20 nm.

13. The catalyst according to claim 1, wherein the optional oxide promoter is vanadium, niobium, tantalum, yttrium, zirconium, antimony, aluminum, boron, thallium or germanium or a mixture thereof.

14. The catalyst according to claim 13, wherein the optional oxide promoter is in the form of promoter salts, organo-promoter compounds and/or organic/inorganic promoter compounds.

15. The catalyst according to claim 13, wherein the oxide promoter, if present, is present is an amount in the range from 0 mol % up to about 4 mol %, based on the amount of the silicon support.

16. A treated noble metal-containing catalyst according to claim 1, wherein the treated noble metal-containing catalyst is used for the oxidation of hydrocarbons.

\* \* \* \* \*